United States Patent [19]

Giegel

[11] Patent Number: 5,250,412
[45] Date of Patent: Oct. 5, 1993

[54] SWAB DEVICE AND METHOD FOR COLLECTING AND ANALYZING A SAMPLE

[75] Inventor: Joseph L. Giegel, Miami, Fla.

[73] Assignee: Diamedix Corporation, Miami, Fla.

[21] Appl. No.: 732,423

[22] Filed: Jul. 16, 1991

Related U.S. Application Data

[63] Continuation of Ser. No. 29,076, Mar. 23, 1987, abandoned.

[51] Int. Cl.$^5$ .................................. G01N 33/53
[52] U.S. Cl. .................. 435/7.1; 435/292; 435/295; 436/807; 436/810; 436/518; 604/1; 604/2
[58] Field of Search ............ 436/531, 161, 807, 808, 436/809, 810, 518, 535, 541, 528, 530; 435/7, 292, 293, 294, 295, 299, 300, 810; 422/58, 69, 100, 101, 102; 210/635, 656, 658, 198.2, 198.3; 604/1, 2, 3

[56] References Cited

U.S. PATENT DOCUMENTS

| | | |
|---|---|---|
| 3,420,205 | 1/1969 | Morison . |
| 3,718,543 | 2/1973 | Lagomarsino ............... 435/292 X |
| 3,792,699 | 2/1974 | Tobin et al. ................ 435/295 |
| 3,798,004 | 3/1974 | Zerachia et al. . |
| 3,811,840 | 5/1974 | Bauer et al. ................. 422/56 |
| 3,954,564 | 5/1976 | Mennen . |
| 4,116,638 | 9/1978 | Kenoff . |
| 4,168,146 | 9/1979 | Grubb et al. . |
| 4,200,625 | 4/1980 | Reese . |
| 4,205,058 | 5/1980 | Wagner et al. ............... 436/810 X |
| 4,235,601 | 11/1980 | Deutsch et al. .............. 436/810 X |
| 4,278,651 | 7/1981 | Hales . |
| 4,338,094 | 7/1982 | Elahi . |
| 4,355,113 | 10/1982 | Mennen ..................... 435/295 |
| 4,366,241 | 12/1982 | Tom et al. .................. 435/7 |
| 4,378,344 | 3/1983 | Zahradnik et al. . |
| 4,391,904 | 7/1983 | Litman et al. . |
| 4,469,787 | 9/1984 | Woods et al. . |
| 4,610,962 | 9/1986 | Takagi et al. . |
| 4,707,450 | 11/1987 | Nason ....................... 435/295 |
| 4,853,325 | 8/1989 | Vodian et al. ............... 435/5 |
| 4,916,056 | 4/1990 | Brown et al. ................ 436/531 |
| 4,978,504 | 12/1990 | Nason ....................... 422/61 |

FOREIGN PATENT DOCUMENTS 0088636 9/1983 European Pat. Off. ............ 436/807

Primary Examiner—James C. Housel
Assistant Examiner—Maureen M. Wallenhorst
Attorney, Agent, or Firm—Willian Brinks Olds Hofer Gilson & Lione

[57] ABSTRACT

A swab device, method, and kit for collecting and analyzing a sample for an analyte (antigens or antibodies) on the swab. The device includes a narrow rod or stick-like support in combination with an assay medium which is positioned adjacent to the support. The assay medium is extended longitudinally down the support a length sufficient to permit an immunoassay to be carried out within it. The assay medium and the support may include a capillary medium. A collection medium may also be attached to the capillary medium to enhance sample collection. The method includes collecting a sample suspected of containing the analyte in a sample collection area at the end of the swab. A liquid containing a labelled component is applied to the swab and allowed to immunochemically react with the sample. If the analyte is present, an immunocomplex is formed and retained on the swab. A wash solution is subsequently applied to the swab to effect the separation of the immunocomplex from excess free label. After separation, the presence or quantity of the analyte in the sample is determined by detecting the label bound to the immunocomplex.

5 Claims, 2 Drawing Sheets

SWAB DEVICE AND METHOD FOR COLLECTING AND ANALYZING A SAMPLE

This application is a continuation, of application Ser. No. 07/029,076, filed Mar. 23, 1987, now abandoned.

BACKGROUND OF THE INVENTION

1. Field of the Invention

The present invention relates to a swab device, a method, and a kit for collecting and performing an immunoassay on a sample for an antigen.

2. Description of the Prior Art

A common method for testing a suspected site of infection for a particular antigen is to swab the area to collect a sample. Once collected, the sample is transferred from the swab to a testing medium wherein an immunoassay is performed to determine the presence of the antigen.

An immunoassay is an indirect measurement of the interaction between an antigen and an antibody to determine the presence or quantity of either material. If a physician suspects that a patient has a strep throat, the physician will swab the patient's throat for streptococcal infections. After the sample is collected, it is transferred from the swab to a test medium by extraction with an extraction reagent. The sample is then assayed for the presence of Strep Group A antigen by a variety of immunochemical methods.

A collected sample must therefore be transferred from the swab to a test medium in order to carry out the assay. To obtain an accurate analysis, the person performing the assay must be cautious not to contaminate the sample while transferring it. Furthermore, extra care must be taken to ensure that the antigen of interest is completely extracted from the swab. Thus, a person must be trained to properly handle a collected sample.

There is a need for a testing device which will eliminate the step of transferring the sample to a test medium after it has been collected. Such a device would allow a sample to be analyzed directly upon it. By integrating the collection and analysis steps, the risk of sample contamination would be greatly reduced while the risk of incomplete transfer would be eliminated. Furthermore, by not requiring a sample to be transferred, untrained personnel would be able to conduct a test more efficiently.

It is therefore an object of the present invention to provide an integrated device for collecting and analyzing a sample for an antigen. It is further an object of the present invention to provide a method for performing an immunoassay for a suspected antigen whereby a sample is collected on a swab and therein an analysis is performed to determine the presence of a suspected antigen. Finally, it is an overall object of the present invention to allow personnel possessing minimal amounts of scientific and laboratory background, training, skill, and experience to perform immunoassays on samples collected by a swab.

SUMMARY OF THE INVENTION

In one embodiment the present invention provides a swab device for collecting a sample and performing an immunoassay thereon. The device integrates the collection and analysis steps thereby simplifying the immunoassay procedure. The device comprises a narrow rod or stick-like support means such as a wood, plastic or cardboard material. A liquid absorbent assay medium such as cotton fiber is positioned adjacent to the support means and is extended longitudinally down the support means. The assay medium extends a length sufficient to permit an immunoassay to be carried out within it.

The extension of the assay medium allows the swab device of the present invention to retain a greater amount of liquid than prior swab devices. When applied to the medium, the liquid separates free label from the immunocomplex thereby allowing label bound to the immunocomplex to be detected without interference from the free label. Thus the assay medium should extend a length sufficient to hold the quantity of liquid necessary to effect the separation of the immunocomplex and free label in the assay medium.

In another embodiment, the present invention provides a swab device for collecting and analyzing a sample wherein the device comprises a collection medium and a capillary medium. The collection medium is positioned adjacent to the capillary medium. In operation, the sample is collected on the collection medium and the analysis is performed. The analysis may be carried out in the collection medium, the capillary medium, or a portion of the analysis may be performed in each.

In yet another embodiment, the present invention provides a swab device for collecting a sample and performing an immunoassay thereon wherein the device comprises an assay medium and a liquid impervious support means. A first portion of the assay medium is enclosed wherein the support means and extended longitudinally down the support means a length sufficient to permit the immunoassay to be carried out within it. A second portion of the assay medium is extended beyond an end of the support means to provide a sample collection area.

In another embodiment, the present invention provides a method for performing an immunoassay on a sample for an analyte wherein the sample is collected and the immunoassay is performed on a single swab device. The swab device comprises an assay medium and a sample is collected on a collection area of the swab. The tip of the collecting end of a swab is contacted with a liquid containing a labelled component. The labelled component immunochemically reacts with the sample to form an immunocomplex which is retained on the swab. The tip of the swab is then contacted with a wash solution and the wash solution is allowed to effect a separation of the immunocomplex from any free label. The label bound to the immunocomplex or the free label may be detected to determine the quantity or quality of analyte present in the sample.

In still another embodiment, the present invention provides a method for performing an immunoassay on a sample for an analyte wherein the sample is collected and the immunoassay is performed on a swab device comprising a capillary medium. The method comprises applying an antianalyte to the capillary medium. A sample suspected of containing an analyte is collected on the collection area of the swab. A wash solution containing a labelled component is applied to the collecting end of the swab and allowed to be drawn by capillary action into the capillary medium wherein the sample, the antianalyte and the labelled component immunochemically react to produce an immunocomplex. The immunocomplex is separated from any free label in the capillary medium by capillary action. The presence or quantity of the analyte in the sample is then determined by detecting either label bound to the immunocomplex or free label.

In a further embodiment, the present invention provides a method for performing an immunoassay on a sample for an analyte wherein the sample is collected and the immunoassay is performed on a swab device comprising a collection medium adjacent to a capillary medium. A sample is collected on the collection medium and a solution containing a labelled component is applied to the collection medium. The sample and the labelled component immunochemically react to form an immunocomplex which is retained in the collection medium. The immunocomplex is separate from excess free label by applying a wash solution to the collection medium. The wash solution carries free label into the capillary medium. The presence or quantity of the analyte is determined by detecting the label bound to the immunocomplex.

The present invention provides a further embodiment for performing an immunoassay on a sample for an analyte wherein the sample is collected and the immunoassay is performed on a swab device comprising a collection medium adjacent to a capillary medium. A sample suspected of containing an analyte is collected on the collection medium. A wash solution is applied to the collection medium to wash the analyte from the collection medium to the capillary medium. The analyte immunochemically reacts with an antianalyte and a labelled component to produce an immunocomplex in the capillary medium. The immunocomplex is separated from any free label by capillary action in the capillary medium. The presence or quantity of the analyte in the sample is determined by detecting either label bound to the immunocomplex or free label.

In yet another embodiment, the present invention provides a capillary medium adapted for receiving a swab such that an immunoassay may be performed on the device when the medium and swab are assembled. The capillary medium contains an internal longitudinal channel which is shaped to receive the support arm of the swab. When fully assembled, the capillary medium is adjacent to the collection medium such that fluid in the collection medium will pass into and be collected by the capillary medium.

In still another embodiment, the present invention provides a kit for performing an immunoassay on a sample for an analyte. The kit comprises a swab device containing an assay medium and a support means wherein the assay medium is adjacent to the support means and extended longitudinally down the support means a length sufficient to permit an immunoassay to be carried out within it. A solution comprising a labelled component and a wash solution are also provided.

DETAILED DESCRIPTION OF THE INVENTION

Figure 1:
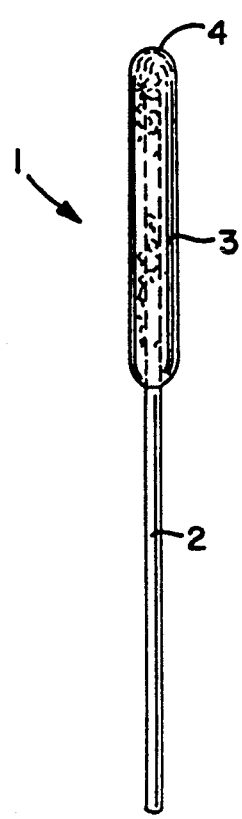
FIG. 1 is a sectional view of a first embodiment of the swab and test device of the present invention wherein an absorbent assay medium is wrapped around a support means.

A novel swab device for collecting a sample and performing an analysis thereon has now been discovered. The term sample is intended to mean a component of interest or analyte, which is to be qualitatively or quantitatively analyzed. The preferred type of analysis employed with the device of the present invention is an assay, and more preferably an immunoassay. A unique feature of the device is that it allows a sample to be collected and analyzed without transferring it from the swab to a testing medium. In other words, the present invention incorporates the test medium into a swab device.

An immunoassay is a test which measures the interaction between an antigen and an antibody. The test can be employed to determine the presence and the quantity of a particular antigen or antibody. An antigen may be any substance which is capable of inducing the formation of antibodies. Antigens may be soluble substances such as toxins and proteins or particulate such as bacteria and tissue cells.

The interaction between antigens and antibodies generally cannot be directly observed. The immunoassay is therefore an indirect method wherein the target of analysis, which can be either an antigen or antibody and is herein referred to as the analyte, is reacted with two substances or reagents to form an immunocomplex.

The first substance, referred to herein as the antianalyte, is any substance which will immunochemically bind with the analyte. Thus, if the analyte is an antigen, the antianalyte is an antibody. Alternatively, if the analyte is an antibody, the antianalyte is an antigen.

The second substance, referred to herein as the labelled component, is any labelled substance which will immunochemically interact with either the analyte or the antianalyte. Thus, the labelled component may be either a labelled analyte (interacting with the antianalyte) or a labelled antianalyte (interacting with the analyte). A labelled analyte may be the same compound as the analyte which is the target of analysis or it may be a compound with similar specificity. A labelled antianalyte is generally a compound which is specific to the analyte of interest.

A label may be any detectable substance which can be coupled to another substance without destroying the individual specificity of the latter substance. Common labels known in the art include, fluorophores, chromophores, enzymes, and radioisotopes.

In a typical immunoassay, a sample, an antianalyte and a labelled component are immunochemically reacted to produce an immunocomplex. If the analyte of interest is present in the sample, the labelled component interacts with the analyte resulting in a portion of the labelled component being bound to the immunocomplex. The relative amount of labelled component bound to the immunocomplex and free labelled component not bound to the immunocomplex is a function of the presence and quantity of analyte in the test sample.

The amounts of bound and unbound or free labelled component are determined by detecting and measuring the label. If the bound labelled component and the free labelled component are essentially indistinguishable by the means employed to measure the label, the bound component and the free component must be physically separated. The type of assay wherein a separation step is required is referred to as a heterogeneous assay.

Though, for simplicity, the present invention may sometimes be generally described in terms of collecting and analyzing a sample for an antigen, it is to be understood that an antibody can also be the analyte. In other words, the component of interest, whether an antigen or antibody, is not to be construed as a limitation of the invention.

The term "analyte" is intended to mean any compound which is the target of analysis in the immunoassay method of the present invention. The analyte may be any substance having antigenic or antibody characteristics or activity. Substances having antigenic characteristics include antigens and haptens. Antigens and haptens are chemical substances which are capable of producing a specific immune response. Antigens may possess any number of valences while haptens are generally considered to be monovalent. The present invention contemplates the use of antigens or haptens as an analyte. Antigenic analyte substances contemplated by the present invention include viruses, bacteria, antibodies, drugs, hormones, and tumor markers.

The present invention also contemplates that an antibody may be the target of analysis. An antibody is generally considered to be any substance that is produced in the body by other cells on contact with an invading foreign microorganism which is acting as an antigen. Antigens generate antibodies which combine specifically with the particular antigen. When a protein has antibody activity, they are often referred to as immunoglobulins. Alternative designations given to these proteins include the term gamma globulin which arose from the observation that the majority of serum antibody molecules migrate electrophoretically in the gamma region. Antibodies contemplated as analytes in the present invention include antibodies to bacteria, viruses, tumors and autoantibodies to normal cellular components.

The term "antianalyte" is intended to mean any substance which will immunochemically react with and bind to the analyte. Thus if the analyte possesses antigenic characteristics, the antianalyte contemplated by the present invention is an antibody that will specifically combine with the antigen. Conversely, if the analyte possesses antibody activity, the present invention contemplates that the antianalyte will possess antigenic characteristics which will cause the antianalyte to specifically bind to the antibody. Specific combinations of analytes and antianalytes contemplated for use in the method of the present invention include herpes and antiherpes antibody.

The term "labelled component" is intended to mean any substance or material having a label attached thereto which will immunochemically interact with either the analyte, antianalyte or immunocomplex. Thus the labelled component may be a labelled analyte. The labelled analyte may be the same compound as the analyte except that a label is attached or it may be a compound or substance with similar specificity with a label attached. A labelled antianalyte may be any compound with a label attached which will specifically interact with and immunochemically bind to the analyte of interest. Whether the labelled component is a labelled analyte or a labelled antianalyte depends upon the immunoassay technique utilized.

A label may be any material which can be coupled to a desired substance without destroying the individual specificity of that substance and yet still yield a detectable parameter. A component may be labelled by any number of ways known in the art. A common way is by the attachment of fluorescent dyes. Such dyes include fluoroscein or rhodamine which can be coupled to a desired substance without destroying the individual specificity. When a fluoroscein label is conjugated to a component, the labelled component can be visualized at the ultraviolet wavelength through the emission of fluorescence. After the immunochemical reaction occurs, the amount of fluorescence detected for either the free labelled component or the bound labelled component is proportional to the quantity of analyte in the liquid sample. A second common means of labelling a component is by the attachment of an enzyme. When the enzyme is allowed to act upon a substrate, a detectable parameter such as a chromophore, is produced. The presence and/or intensity of color produced by either an enzyme label bound to an immunocomplex formed or a free enzyme labelled material can be visually detected. The concentration of analytes present in the liquid sample is a function of the amount of chromophore detected.

Labelling components contemplated by the present invention include chemiluminescent compounds, radioactive compounds, and the like. Enzyme materials contemplated for use as labels in the present invention include alkaline phosphatase and peroxidase. Substrates which are contemplated by the present invention and are acted upon by the enzyme labels include p-nitrophenyl phosphate and indoxyl phosphate.

The term "immunocomplex" is intended to mean any complex resulting from the interaction of the analyte, the antianalyte, or labelled component in any combination or order. The term "immunochemical reaction" refers to the interaction between the analyte, antianalyte or labelled component. Depending upon the immunoassay technique employed, an analyte may interact with an antianalyte, an analyte may interact with a labelled component, or an antianalyte may interact with a labelled component to form an immunocomplex. Furthermore, an immunocomplex may be formed by an analyte binding with either an antianalyte or a labelled component, or it may be formed by the displacement of a labelled component from an immunocomplex containing an antianalyte and a labelled component. In addition, the formation of an immunocomplex may be a reversible reaction.

The invention also contemplates a wash solution which may be any liquid which sufficiently carries excess free label through the assay medium. Preferably, the wash solution is water for fluorescent labels. In another embodiment, the present invention contemplates a wash solution containing a substrate of the enzyme. The enzyme and substrate react to produce an enzyme-substrate detectable parameter. The presence of analyte in the sample is determined by detecting the enzyme-substrate detectable parameter produced from bound enzyme label. A second enzyme-substrate detectable parameter may be produced by excess free enzyme label. This latter parameter, however, does not interfere with detection of the bound enzyme label because the immunocomplex and free label are previously separated. Substrates further contemplated by the present invention and the acting enzymes include 4 methyl umbelliferone phosphate for alkaline phosphatase.

Prior to detection of bound label, the immunocomplex and excess free label must be separated. Thus, to carry out an immunoassay in the assay medium, the medium must retain a quantity of liquid sufficient to effect the separation of the immunocomplex and free label.

The immunocomplex and free label may be separated by either a solid phase or a liquid phase separation. In a solid phase separation, the assay medium retains the immunocomplex while the free label is washed away. The immunocomplex may be retained by immunologically immobilizing it to the assay medium or by trapping it within the voids of the assay medium.

A liquid phase separation, however, does not require the assay medium to immobilize the immunocomplex. In a liquid phase separation, the difference in capillary flow between two substances enables their separation. In the present invention, the capillary flow of the immunocomplex is impeded in relation to the free label. By maintaining capillary action with a sufficient quantity of liquid, the disparity in capillarity between the immunocomplex and free label causes bound and free label to separate.

In the present invention, the immunocomplex and the free label may be separated by either a solid phase or a liquid phase separation. Thus, depending upon the material employed, the immunocomplex may be trapped by the assay medium thereby effecting a solid phase separation or the capillary action of the immunocomplex may be impeded by the assay medium thereby effecting a liquid phase separation. In the latter instance, the capillary action of free label in the medium would be greater than that of the immunocomplex. By applying a sufficient quantity of liquid, the free label separates from the immunocomplex. Thus regardless of the type of separation, the assay medium is extended longitudinally down the support means a length sufficient to provide the area or volume of assay medium necessary to retain the amount of liquid required to effect the separation of the immunocomplex and free label.

The principles of solid phase and liquid phase separation, and the differences between the two techniques are extensively discussed in my copending application entitled "Heterogeneous Immunoassay System and Method," the complete teachings of which are incorporated herein by reference.

The swab device of the present invention may be employed with a number of assay techniques. Most common of the immunoassay techniques are the competitive assay and the sandwich assay. In the competitive assay, the liquid sample containing the analyte is contacted with a mixture of antianalyte and labelled analyte. The concentration of the antianalyte and the labelled analyte are chosen such that when the unlabelled analyte is added, the labelled analyte and unlabelled analyte compete to form an immunocomplex with the antianalyte. In the case of a heterogeneous immunoassay, a competitive type assay may be conducted by first coating a solid phase with a mixture of antianalyte and labelled analyte to form an immunocomplex. Knowing the concentration of the antianalyte and labelled analyte, the unlabelled analyte can then be applied to this zone and allowed to displace a portion of the labelled analyte from the immunocomplex. The amount of labelled analyte displaced is a function of the quantity of unlabelled analyte.

The present invention enables a sample to be collected and analyzed on the same swab device. Integrating these functions is accomplished by providing a volume of assay medium sufficient to permit an immunoassay to be carried out within it.

The absorbent assay medium contemplated by the present invention may be any material capable of carrying a liquid when contacted therewith. The assay medium may thus carry liquids by capillary action or by sorption. Suitable assay mediums include absorbent materials such as cotton, fibrous mediums, microporous and cellulosic membranes. Furthermore, the assay medium may be a combination of two or more materials. For example, cotton may be combined with a capillary medium. Preferred assay mediums include cotton fiber and capillary mediums.

The support means is preferably constructed of a long, thin, resilient material. The support means may be in the shape of a bar, rod or stick and may function as a holder for the absorbent assay medium. Suitable materials contemplated for use as a support means include wood, cardboard, plastic, and other resinous materials. The support means may also be capable of carrying a liquid. For example, a rod or bar shaped capillary medium may function as the support means.

The assay medium and support means of the swab device may be constructed from the same or different materials. When constructed of the same materials, one embodiment of the present inventions allows the assay medium and support means to be combined in a single unit. For example, a rod-shaped capillary medium having sufficient rigidity may function as a support means and assay medium.

In another embodiment, the assay medium may be positioned adjacent to the support means. This may be accomplished by wrapping the assay medium around, attaching it to the end of the support means, or adapting the medium to receive the support means.

In still another embodiment, the assay medium may be positioned adjacent to the support means by enclosing it within the support means.

In a still further embodiment, the swab device of the present invention may also contain a collection medium to enhance sample collection. The collection medium may be constructed of any absorbent material such as fibrous mediums, microporous and cellulosic membranes, cotton, and filter paper. The collection medium may function as the assay medium in whole or in combination with a capillary medium.

Capillary mediums contemplated by the present invention may be any material capable of carrying a liquid by capillary action when contacted therewith. Suitable capillary mediums include porous materials having connecting voids, bibulous materials, cloths, cellulosic paper, glass filter materials and, microporous membranes. The capillary medium may comprise any one or a combination of these porous materials. Presently preferred are capillary mediums comprising a cellulosic microporous membrane. A most preferred capillary medium is a cylindrical shaped medium commercially sold by Porex and is available as a rod-shaped device.

The capillary medium may possess various physical and chemical characteristics. For example, the void spaces may be of a size sufficiently small to trap interfering materials but sufficiently large to allow passage of the remainder of the liquid therethrough. The capillary medium may also possess void spaces of a size sufficient to cause the capillary action of one substance to be impeded (but not immobilized) in relation to the capillary action of another substance. The disparity in capillarity between two substances in a capillary medium is sufficient to effect a liquid phase separation of the substances. Differences in capillarity may also be caused by molecular forces between the medium and the substance molecules.

One advantage of a liquid phase separation is that reactants need not be immobilized to effectively separate bound label from free label. The only requirement is that the substances to be separated have different capillarities. In other words, the capillary action of one substance should be impeded in relation to the other. The means by which a substance is impeded in its motion through the capillary medium is not essential to the invention. In the liquid phase separation embodiment, the invention only contemplates that either the bound label attached to the immunocomplex or the free label in solution be impeded in relation to the other in some manner. Preferably, the capillarity of the bound label attached to the immunocomplex is impeded.

The present invention contemplates capillary medium void space sizes of up to 40 microns. The exact preferred size range depends upon the type of analyte being analyzed and the type of antianalyte and labelled component employed. Furthermore, the present invention contemplates the removal of materials such as particulate matter which may interfere with the analysis. The size range may therefore also be a function of the size and type of interfering material to be removed. A capillary medium void space size range of up to 10 microns is currently preferred. A more preferred capillary void space size range is about 0.5 to 5 microns.

The capillary medium may also be adapted to receive the support means of a swab. Any means for adapting the capillary medium to the support means is contemplated. Preferably, the medium will contain a longitudinal channel, groove or cavity which will receive the swab support such that when fully assembled, the capillary medium is abutted or adjacent to the collection medium of the swab. By being adjacent, fluid may pass from the collection medium into and be collected by the capillary medium. Thus, the channel may be annular-shaped and therefore joined with the support by being slid over the support in a sleeve-like fashion.

The capillary medium may also contain a longitudinal slit cut into the capillary medium to form an internal channel. In this instance, the capillary medium may be snapped or clipped onto the swab support and adjusted to be adjacent to the collection medium.

In use, the medium may be attached to the swab after the sample is collected on the collection medium. Alternatively, immunoreagents may be added to the collected sample and allowed to incubate or immunologically react with the sample. Thereafter, the capillary medium may be attached to the swab support. In any event, the attached capillary medium increases the volume of the assay medium sufficient to permit an immunoassay to be carried out within the assembled swab device.

In another embodiment of the present invention, a method for collecting and analyzing an analyte on a single swab device is contemplated. A preferred method of analysis is the immunoassay. In one embodiment of the method of the present invention, a sample may be collected in a sample collection area by scraping or swabbing a sample site with the tip of the swab device. A liquid containing an antianalyte to the analysis is applied to the swab near or at the point of collection. The liquid may also contain materials such as detergents, enzymes, etc. to expose the analyte to the antianalyte. The liquid is allowed to enter the area where the sample is present. If the analyte is present in the sample, the antianalyte present in the liquid binds with the analyte to form an immunocomplex which is retained in the assay medium. A liquid solution containing a labelled component may then be applied to the swab and allowed to immunologically react with the immunocomplex, thereby causing some label to bind to the immunocomplex. The immunocomplex and excess free label are separated by applying a wash solution. The wash solution carries excess free label away from the immunocomplex and down the assay medium thereby separating free and bound label. By extending the assay medium longitudinally down the support means, the swab device is able to retain the quantity of wash solution necessary to effect the separation. The presence or quantity of the analyte may be determined by detecting the label bound to the immunocomplex.

Where the label is an enzyme, the wash solution may comprise a substrate to the enzyme. The substrate in the wash solution reacts with the enzyme to produce an enzyme-substrate detectable parameter. The presence of the analyte in the sample is determined by detecting the enzyme-substrate detectable parameter produced by the bound enzyme label. A second enzyme-substrate detectable parameter may be produced by excess free enzyme label. This latter parameter, however, will not interfere with detection of the bound enzyme label because the immunocomplex and free label have been previously separated.

In another embodiment, the present invention contemplates a method of collecting a sample and performing an immunoassay for an analyte with a swab device comprising a capillary medium. In this embodiment, an antianalyte may be pre-coated on the capillary medium at or near the point where the sample is to be collected. The sample is collected in a sample collection area by scraping or swabbing the sample site with an end of the swab device. A liquid is then applied to the capillary medium to carry the sample through the capillary medium by capillary action where it contacts and immunochemically reacts with the antianalyte. If the analyte is present in the sample, an immunocomplex is formed. The immunocomplex may then be allowed to immunochemically react with a labelled component thereby causing some label to bind to the immunocomplex. The labelled component may be applied to the capillary medium either before collection of the sample, with the antianalyte, or after applying the antianalyte. Regardless of when the labelled component is applied, the difference in capillary action between the immunocomplex and any excess free label will cause a separation.

By applying sufficient liquid to the capillary medium, the immunocomplex separates from excess free label in the liquid phase. The separation may be achieved by applying the liquid which contains the labelled component or by applying an additional wash solution such as water. After separation, the presence or quantity of the analyte may be determined by detecting the label bound to the immunocomplex.

Where the label is an enzyme, the present invention contemplates applying a wash solution containing a substrate of the enzyme. The substrate reacts with the enzyme to produce an enzyme-substrate detectable parameter. The presence or quantity of the analyte in the sample may then be determined by detecting the enzyme-substrate detectable parameter produced by the bound enzyme label. A second enzyme-substrate detectable parameter may be produced by excess free enzyme label. This latter parameter, however, will not interfere with detection of the bound enzyme label because the immunocomplex and free label have been previously separated.

In yet another embodiment, the present invention further contemplates attaching a collection medium at the end of the capillary medium to enhance sample collection. The collection medium may function as an assay medium, in whole or in combination with the capillary medium. The sample may be retained in the collection medium, thereby permitting a solid phase separation of bound and free label. Conversely, the sample may be washed through the collection medium into the capillary medium. In the latter instance, the immunocomplex is formed and separated from free label by a liquid phase separation in the capillary medium.

The label or detectable parameter produced may be measured by various means. The preferred and simplest form of detection is by visual inspection. The invention, however, also contemplates the use of spectrophotometric and radiometric instrumentation. A preferred detection instrument is a fluorometer. A fluorometer operates by producing a light at a specified wavelength range. The light is passed through a series of filters to select a predetermined range of wavelengths which are transmitted to the medium to be analyzed. The transmitted light is absorbed by the previously labelled reaction product and subsequently emits a detectable spectra which indicates the presence or quantity of analyte in a sample.

In still another embodiment, the present invention contemplates a system or kit which includes a swab device of the present invention, a solution comprising an antianalyte, a solution comprising a labelled component, and a wash solution. The swab device may comprise any one of the embodiments discussed in the specification. Furthermore, the labelled component solution may comprise an enzyme label while a substrate may be solubilized in the wash solution or in an additional substrate solution. The solution containing the antianalyte may also contain the labelled component.

The system or kit may also include means for detecting the results of the immunoassay. For example, colorimeters or fluorometers may be included. If visual inspection is required, comparable color charts may also be included. The particular detection instrumentation, however, is not essential to the invention. Those skilled in the art will readily recognize that any suitable means for detecting the results of the analysis may be employed.

Additional embodiments of the present invention which are obvious to those skilled in the art are also contemplated. The following drawings and examples are not intended to be a limitation on the scope of the invention.

DETAILED DESCRIPTION OF THE DRAWINGS

FIG. 1 illustrates one embodiment of the present invention. The swab device 1 comprises a support means 2 and an assay medium 3. The support means 2 may be constructed of any lightweight resilient material. Contemplated materials include wood, cardboard, plastic, and resinous materials. The support means 2 may also be constructed of a cellulosic membrane capillary medium. The assay medium 3 is attached longitudinally to the support means 2 by wrapping it around a portion of the support means 2. The assay medium 3 is extended longitudinally down the support means 2 a length sufficient to permit an immunoassay to be carried out on the swab device 1. The assay medium 3 is constructed of any absorbent material and may also be a capillary medium. The most preferred absorbent material is cotton.

In one embodiment of the method contemplated by the present invention, a sample suspected to contain an antigen may be collected at or near the end of the swab device 1 in the sample collection area 4. A solution containing labelled antibody to the antigen of interest is applied to the assay medium 3 at or near the sample collection area 4. Preferably the labelled antibody is applied by dipping the tip of the sample collection area 4 into the solution. The labelled antibody solution migrates into the assay medium 3 and contacts the sample in sample collection area 4. If the antigen of interest is present, the labelled antibody immunochemically reacts with the antigen to form an immunocomplex. The immunocomplex formed is retained in the sample collection area 4 of the assay medium 3.

A wash solution is then applied to the assay medium 3. Preferably the wash is applied by dipping the tip of the sample collection area 4 of the assay medium 3 into the solution. The wash solution migrates into the assay medium 3. As the wash solution migrates through the assay medium 3 excess free labelled antibody is washed away from the immunocomplex thereby separating the bound and free label. The wash solution is applied in an amount sufficient to carry free label down the assay medium 3 and away from the immunocomplex in sample collection area 4. After separation, the presence or quantity of antigen in the sample may be determined by detecting the label bound to the immunocomplex.

Figure 2:
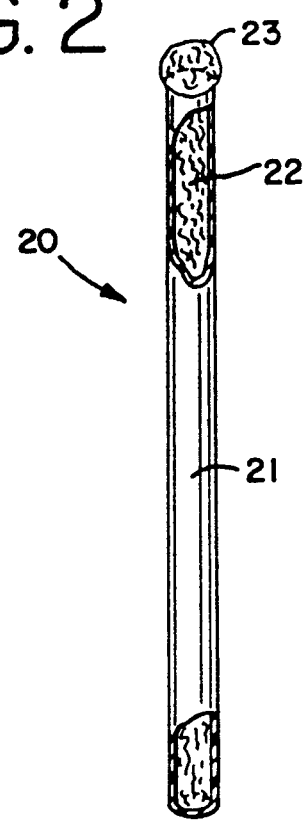
FIG. 2 is a sectional view of a second embodiment of the swab and test device of the present invention wherein an absorbent assay medium is enclosed by a support means.

A further embodiment of the swab device of the present invention is depicted in FIG. 2. The swab device 20 comprises a support means 21 and a assay medium 22. The swab device of FIG. 2 is similar to the device of FIG. 1 in that the assay medium 22 is extended down the support means a length sufficient to permit an immunoassay to be carried out on the swab device 20. The swab device of FIG. 2 differs from the device of FIG. 1 in that the assay medium 22 is enclosed by the support means 21. A sample collection area 23 is provided by maintaining a portion of the assay medium 22 above or beyond the end of support means 21. The swab device of FIG. 2 may be employed for collecting and analyzing a sample in accordance with any of the method embodiments contemplated.

Figure 3:
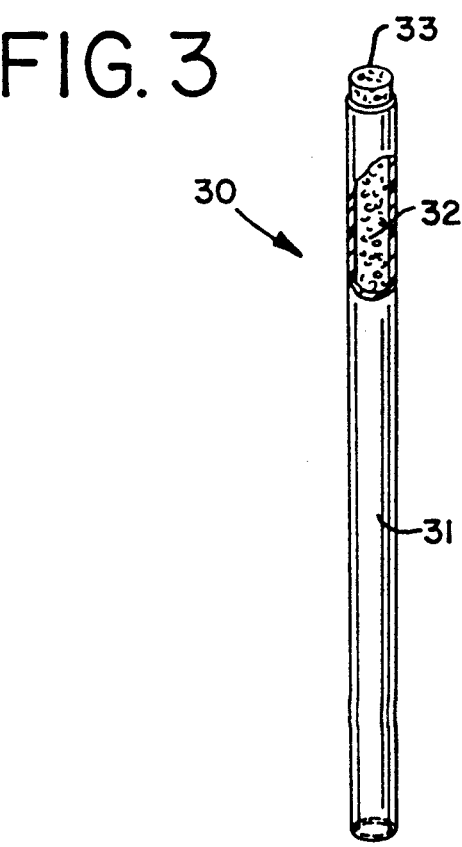
FIG. 3 is a sectional view of a third embodiment of the swab and test device of the present invention wherein a support means comprises a capillary medium.

FIG. 3 depicts a further embodiment of the swab device of the present invention. The swab device 30 comprises a capillary medium 32 surrounded by a liquid impervious enclosure 31. The capillary medium 32 and liquid impervious enclosure 31 function as a support means for the swab device 30. The capillary medium further functions as the assay medium. The liquid impervious enclosure 31 is preferably a clear, thin material which is wrapped around the capillary medium 32. The liquid impervious enclosure 31 provides strength and rigidity to the swab device 30 and retains liquid in the capillary medium 32. A sample collection area 33 is provided by maintaining a portion of the capillary medium 32 above or beyond the liquid impervious enclosure 31.

In another method embodiment contemplated by the invention, a sample suspected of containing an antigen is collected on the end of the swab device 30 at sample collection area 33. A liquid solution containing a labelled antibody to the antigen of interest is applied to the capillary medium 32 at or near the sample collection area 33. If the antigen is present the labelled antibody immunochemically reacts with the antigen to form an immunocomplex in the capillary medium 32 containing bound label. As the liquid, the immunocomplex, and any excess labelled antibody migrate through the capillary medium by way of capillary action, the immunocomplex may be immunochemically reacted with a second antibody to the antigen of interest thereby forming a second immunocomplex. The second antibody may be applied to the capillary medium either before, during or after collection of the sample or application of the labelled antibody. Regardless of when the second antibody is applied, the capillary action of the second immunocomplex is impeded in relation to any excess free labelled antibody.

As additional liquid is applied to the capillary medium 32, the second immunocomplex and the free labelled antibody separate in the liquid phase because of the difference in capillarity. The additional liquid applied may be a solution containing the second antibody or may be a wash solution such as water. If the label is an enzyme, the wash solution may contain a substrate. The liquid phase separation separates label bound to the immunocomplex from free label. After the separation, the presence or quantity of antigen in the sample may be determined by detecting the label bound to the second immunocomplex.

Figure 4:
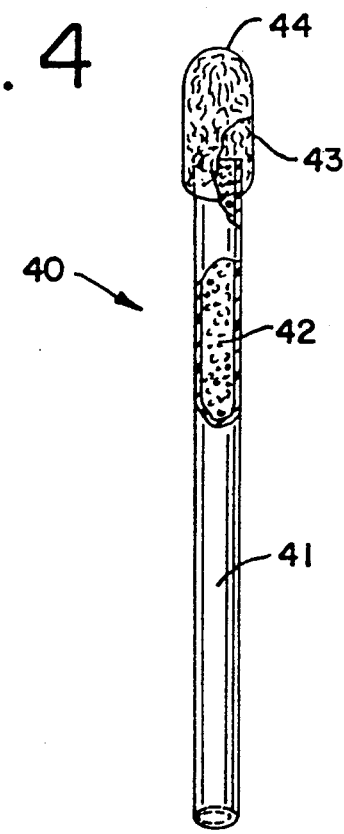
FIG. 4 is a sectional view of a fourth embodiment of the swab and test device of the present invention wherein a collection medium is wrapped around a support means comprising a capillary medium.

FIG. 4 depicts another embodiment of the swab device of the present invention. The swab device 40 comprises a capillary medium 42 surrounded by a liquid impervious enclosure 41. The capillary medium 42 and liquid impervious enclosure 41 function as a support means for the swab device 40. To enhance sample collection a collection medium 43 is attached at or near the end of the swab device 40. The capillary medium 42 in combination with the collection medium 43 function as the assay medium.

This embodiment may be employed by collecting a sample suspected of containing an antigen on the collection medium 43 at or near the sample collection area 44. A liquid containing labelled antibody is then applied to the swab device at or near the sample collection area 44. If antigen is present in the sample, the labelled antibody immunochemically reacts with the antigen to form an immunocomplex which is retained in the collection medium 43. Additional wash solution may be applied to the sample collection area 44 to effect a solid phase separation of the immunocomplex from any free labelled antibody. As liquid is applied, it passes through the collection medium 43 and accumulates in capillary medium 42. The presence of antigen is then determined by detecting the label bound to the immunocomplex in collection medium 43.

The present invention also contemplates a liquid phase separation of the immunocomplex and free label. In this embodiment, before the labelled antibody is applied, the sample is washed from the collection medium 43 into the capillary medium 42. Once in the capillary medium, liquid reagents may be reacted with the sample to form an immunocomplex having impeded capillarity in relation to free label. As described under FIG. 3, the difference in capillarity between the immunocomplex and free label will promote the liquid phase separation of bound and free label. The presence or quantity of antigen may be determined by detecting the label bound to the immunocomplex.

Figure 5:
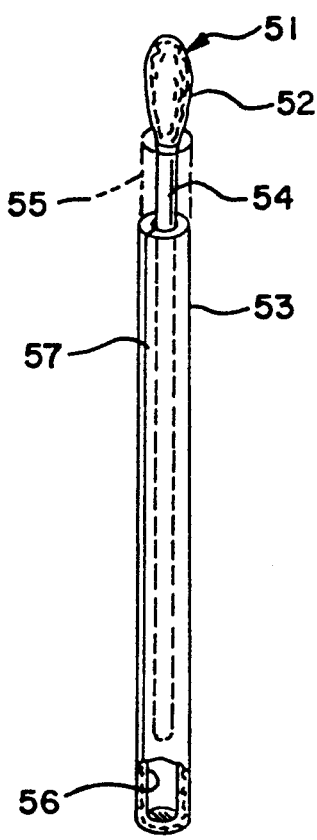
FIG. 5 is a sectional view of a fifth embodiment of the swab and test device of the present invention wherein a capillary medium is adapted to receive the support means of a swab through a longitudinal channel in the medium.

FIG. 5 depicts yet another embodiment of the swab device of the present invention. A sample suspected of containing an analyte may be collected in the sample collection area 51 of collection medium 52. A liquid containing a labelled component may then be applied to the collection medium 52 at or near the sample collection area 51. A rod-shaped capillary medium 53 adapted for receiving the swab support 54 is joined with the support such that it is adjacent with the lower portion of the collection medium 52 as indicated by the phantom position 55. The capillary medium may be attached either directly after the sample is taken or after the labelled component is added and allowed to incubate on the collection medium. In any event, once the capillary medium is attached, a wash solution and other immunoreagents such as antianalytes may be applied as needed to carry out the immunoassay.

The capillary medium is joined with the support and collection medium in such a manner that it will receive and collect excess fluid such as the wash solution added to the collection medium. Thus, after a sample is taken, an immunoassay can be quickly and easily performed. Those skilled in the art will recognize that the capillary medium may be any shape which will allow an immunoassay to be performed as described herein. Preferably, the capillary medium is rod-shaped. In addition, it is to be understood that the capillary medium may be attached to the support and abutted to the collection medium by any suitable means. Preferably, as illustrated, the capillary medium contains a channel 56 which may be slid onto and over the swab support 54 in a sleeve-like fashion. Alternatively, the capillary medium may take the same cylindrical shape as illustrated at 53, but instead of being slid onto the swab, is either rolled or wrapped around the swab. Furthermore, a cylinder shaped capillary medium may contain a longitudinal slit 57 and then inserted or snapped onto the swab support 54 and adjusted to be adjacent to the collection medium 52.

EXAMPLES

EXAMPLE 1

A device as shown in FIG. 1 is constructed of a wooden solid support covered with cotton fibers. This is similar to the standard swabs used for sample collections, however, additional cotton is added to increase the fluid holding capacity. The swab may be used to check for the presence of streptococci in throat infections. The throat is swabbed in the normal manner using this device. Subsequently the tip of the swab containing the area where antigen may be present is immersed briefly in a small volume of enzyme labelled antibody (conjugate) to streptococci. The volume of conjugate used is not sufficient to fully wet the swab. The conjugate may contain surface active agents or detergents to make the strep antigen more readily available to the antibody. After a brief incubation the tip of the swab is then immersed in a colorimetric substrate for the enzyme. The substrate travels up through the swab, washing away label which is not bound to antigen. If antigen is present on the tip of the swab, a color will develop as a result of the enzyme activity. The swab is then inspected visually.

EXAMPLE 2

The swab device in FIG. 2 is constructed from a hollow concentric plastic material to provide rigidity to the collection device. The interior of the device is filled with cotton or cellulose acetate fibers. This device is used to examine for the presence of herpes antigen in a lesion. In use, the tip of the swab is contacted with the fluid from a suspected herpatic lesion. If the herpes antigen is present, it will bind non-specifically to the fibrous materials at the tip. Subsequently, the tip is immersed in antibody to herpes labelled with fluorescin. If the virus is present on the fibers, the antibody will bind. Subsequently, the tip is immersed in an aqueous wash fluid. As the fluid travels up the device, it will wash away any labelled antibody which is not bound to the antigen in the tip. For reading, the device is viewed under a UV lamp and the presence of fluorescence will indicate that the antigen is present in the lesion.

EXAMPLE 3

The device in FIG. 3 is constructed of a porous plastic material which is rigid, but possesses capillary action. This device is used to detect the presence of herpes virus in a suspected lesion by contacting the tip of the device with the lesion, allowing the viral antigen to be attached to the plastic structure. The tip is then immersed in enzyme labelled antibody to herpes, allowed to incubate for a brief interval and then immersed in substrate for the enzyme. The substrate will travel through the capillary medium carrying with it unbound antibody and allowing visualization of the bound antibody at the tip of the device. The substrate may either be colorimetric or fluorogenic and the presence of virus can be examined either by fluorescence or by visual inspection.

EXAMPLE 4

The device shown in FIG. 4 consists of a rigid capillary medium covered with a cotton fiber. Cotton fiber is the accepted material used for collection of specimens. In use, the device is used to scrape suspected areas of streptococcus in the throat. The tip is then immersed in a small volume of enzyme labelled antibody to streptococci and subsequently immersed in the substrate for the enzyme. The substrate will travel up the capillary device moving the unbound fraction with it, thus providing a means for visualizing the antigen.

I claim:

1. A method for performing an immunoassay for an analyte with a swab, said method comprising:
   a) providing a swab without initial specific binding characteristics and comprising an absorbent means and a support means, said absorbent means having a first area for collecting a sample at a distal end and a second area for retaining liquid extending longitudinally down the support means a length sufficient to permit an immunoassay to be carried out within the absorbent means;
   b) collecting a sample containing the analyte on the collecting area of the absorbent means;
   c) thereafter adding a labelled component to the absorbent means, the labelled component being specific to the analyte;
   d) immunochemically reacting the labelled component and the analyte to form an immunocomplex and allowing the immunocomplex to become physically trapped in the absorbent means;
   e) separating the trapped immunocomplex from unreacted labelled component by capillary action of the absorbent means; and
   f) detecting the analyte by detecting the label specifically bound to the trapped immunocomplex or detecting the free label not specifically bound and which has been separated from the trapped immunocomplex.

2. The method of claim 1 further comprising the step of extracting the analyte from any interfering material after the collection of sample onto the absorbent means of the swab and prior to adding the labelled component.

3. A method for performing an immunoassay for an analyte with a swab, said method comprising:
   a) providing a swab without initial specific binding characteristics and comprising an absorbent means and a support means, said absorbent means having a first area for collecting a sample at a distal end and a second area for retaining liquid extending longitudinally down the support means a length sufficient to permit an immunoassay to be carried out within the absorbent means;
   b) collecting a sample containing the analyte on the collecting area of the absorbent means;
   c) thereafter adding a labelled component to the absorbent means, the labelled component being specific to the analyte;
   d) immunochemically reacting the labelled component and the analyte to form an immunocomplex and allowing the immunocomplex to become physically trapped in the absorbent means;
   e) adding a wash solution to the absorbent means to separate the trapped immunocomplex from any unreacted labelled component; and
   f) detecting the analyte be detecting the label specifically bound to the trapped immunocomplex or detecting the free label not specifically bound and which has been separated from the trapped immunocomplex.

4. The method of claim 3 wherein the label is an enzyme and the wash solution contains a substrate of the enzyme.

5. A method for performing an immunoassay for an analyte with a rod-shaped absorbent assay medium, said method comprising:
   a) providing a rod-shaped absorbent assay medium without initial specific binding characteristics and comprising a support means, said absorbent medium having a first area for collecting a sample at a distal end and a second area for retaining liquid used in an immunoassay;
   b) collecting a sample containing the analyte on the collection area of the absorbent medium;
   c) thereafter adding a labelled component to the absorbent medium, the labelled component being specific to the analyte;
   d) immunochemically reacting the labelled component and the analyte to form an immunocomplex and allowing the immunocomplex to become physically trapped in the absorbent medium;

e) separating the trapped immunocomplex from unreacted labelled component by capillary action of the absorbent medium; and f) detecting the analyte by detecting the label specifically bound to the trapped immunocomplex or detecting the free label not specifically bound and which had been separated from the trapped immunocomplex.

* * * * *